(12) United States Patent
Willyard et al.

(10) Patent No.: US 10,335,230 B2
(45) Date of Patent: Jul. 2, 2019

(54) SYSTEMS FOR THERMAL-FEEDBACK-CONTROLLED RATE OF FLUID FLOW TO FLUID-COOLED ANTENNA ASSEMBLY AND METHODS OF DIRECTING ENERGY TO TISSUE USING SAME

(75) Inventors: Richard A. Willyard, Longmont, CO (US); Joseph D. Brannan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 1124 days.

(21) Appl. No.: 13/043,665

(22) Filed: Mar. 9, 2011

(65) Prior Publication Data

US 2012/0232544 A1 Sep. 13, 2012

(51) Int. Cl.
*A61B 18/00* (2006.01)
*A61B 18/18* (2006.01)

(52) U.S. Cl.
CPC ...... *A61B 18/1815* (2013.01); *A61B 2018/00023* (2013.01); *A61B 2018/00166* (2013.01); *A61B 2018/00744* (2013.01); *A61B 2018/00791* (2013.01); *A61B 2018/00863* (2013.01); *A61B 2018/00898* (2013.01); *A61B 2018/1869* (2013.01)

(58) Field of Classification Search
CPC ........... A61B 2018/00005; A61B 2018/00011; A61B 2018/00166; A61B 2018/00636; A61B 2018/00714; A61B 2018/00744; A61B 2018/00791–2018/821; A61B 2018/00831; A61B 2018/1472
USPC ............................ 606/33, 20–52; 607/1–156
See application file for complete search history.

(56) References Cited

U.S. PATENT DOCUMENTS

| | | | |
|---|---|---|---|
| D223,367 S | 4/1972 | Kountz | |
| 3,823,575 A | * 7/1974 | Parel | .............................. 62/51.2 |
| D263,020 S | 2/1982 | Rau, III | |

(Continued)

FOREIGN PATENT DOCUMENTS

| | | |
|---|---|---|
| CN | 1103807 | 6/1995 |
| DE | 390937 | 3/1924 |

(Continued)

OTHER PUBLICATIONS

European Search Report for European Application No. 12001643.1 dated Jun. 1, 2012.

(Continued)

*Primary Examiner* — Ronald Hupczey, Jr.

(57) ABSTRACT

A method of directing energy to tissue using a fluid-cooled antenna assembly includes the initial step of providing an energy applicator. The energy applicator includes an antenna assembly and a hub providing at least one coolant connection to the energy applicator. The method also includes the steps of providing a coolant supply system including a fluid-flow path fluidly-coupled to the hub for providing fluid flow to the energy applicator, positioning the energy applicator in tissue for the delivery of energy to tissue when the antenna assembly is energized, and providing a thermal-feedback-controlled rate of fluid flow to the antenna assembly when energized using a feedback control system operably-coupled to a flow-control device disposed in fluid communication with the fluid-flow path.

13 Claims, 7 Drawing Sheets

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| 4,741,348 A | 5/1988 | Kikuchi et al. | |
| 4,744,372 A | 5/1988 | Kikuchi et al. | |
| 4,747,416 A | 5/1988 | Kikuchi et al. | |
| 5,084,044 A | 1/1992 | Quint | |
| 5,129,396 A | 7/1992 | Rosen | |
| 5,300,099 A * | 4/1994 | Rudie | A61B 18/18 604/20 |
| 5,342,357 A | 8/1994 | Nardella | |
| D354,218 S | 1/1995 | Van de Peer | |
| 5,437,629 A * | 8/1995 | Goldrath | 604/21 |
| 5,462,521 A | 10/1995 | Brucker et al. | |
| 5,535,818 A | 7/1996 | Fujisaki et al. | |
| 5,569,188 A * | 10/1996 | Mackool | 604/67 |
| 5,643,197 A | 7/1997 | Brucker et al. | |
| 5,879,347 A * | 3/1999 | Saadat | A61B 17/42 604/113 |
| 6,007,571 A | 12/1999 | Neilson | |
| 6,039,728 A | 3/2000 | Berlien et al. | |
| D424,693 S | 5/2000 | Pruter | |
| D424,694 S | 5/2000 | Tetzlaff et al. | |
| D425,201 S | 5/2000 | Tetzlaff et al. | |
| 6,059,780 A * | 5/2000 | Gough et al. | 606/42 |
| 6,203,541 B1 * | 3/2001 | Keppel | 606/38 |
| 6,223,085 B1 | 4/2001 | Dann | |
| D449,886 S | 10/2001 | Tetzlaff et al. | |
| 6,334,074 B1 * | 12/2001 | Spertell | 607/101 |
| D457,958 S | 5/2002 | Dycus et al. | |
| D457,959 S | 5/2002 | Tetzlaff et al. | |
| 6,413,255 B1 | 7/2002 | Stern | |
| 6,500,175 B1 | 12/2002 | Gough et al. | |
| 6,575,969 B1 | 6/2003 | Rittman, III | |
| 6,592,577 B2 | 7/2003 | Abboud et al. | |
| 6,635,053 B1 * | 10/2003 | Lalonde et al. | 606/22 |
| D487,039 S | 2/2004 | Webster et al. | |
| 6,702,810 B2 | 3/2004 | McClurken et al. | |
| 6,743,184 B2 * | 6/2004 | Sampson et al. | 600/560 |
| 6,780,184 B2 * | 8/2004 | Tanrisever | 606/45 |
| D496,997 S | 10/2004 | Dycus et al. | |
| D499,181 S | 11/2004 | Dycus et al. | |
| 7,018,398 B2 * | 3/2006 | Eshel | 607/96 |
| 7,022,121 B2 * | 4/2006 | Stern et al. | 606/41 |
| 7,060,062 B2 * | 6/2006 | Joye et al. | 606/21 |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,255,680 B1 * | 8/2007 | Gharib | 604/67 |
| 7,311,703 B2 | 12/2007 | Turovskiy et al. | |
| D564,662 S | 3/2008 | Moses et al. | |
| D576,932 S | 9/2008 | Strehler | |
| 7,422,587 B2 * | 9/2008 | Bek et al. | 606/41 |
| D594,736 S | 6/2009 | Esjunin | |
| D594,737 S | 6/2009 | Kelly et al. | |
| 7,585,296 B2 * | 9/2009 | Edwards et al. | 606/41 |
| 7,604,631 B2 * | 10/2009 | Reynolds | 606/20 |
| D606,203 S | 12/2009 | Husheer et al. | |
| D613,412 S | 4/2010 | DeCarlo | |
| D634,010 S | 3/2011 | DeCarlo | |
| 8,187,261 B2 * | 5/2012 | Watson | A61M 25/1006 606/21 |
| 8,372,067 B2 * | 2/2013 | Woloszko et al. | 606/34 |
| 8,702,693 B2 * | 4/2014 | Subramaniam | A61B 18/1206 604/28 |
| 2004/0143250 A1 * | 7/2004 | Trembly | 606/33 |
| 2005/0015081 A1 | 1/2005 | Turovskiy | |
| 2005/0033278 A1 | 2/2005 | McClurken et al. | |
| 2005/0065584 A1 | 3/2005 | Schiff et al. | |
| 2005/0149010 A1 | 7/2005 | Turovskiy et al. | |
| 2005/0245920 A1 | 11/2005 | Vitullo | |
| 2006/0015162 A1 * | 1/2006 | Edward et al. | 607/105 |
| 2007/0142829 A1 | 6/2007 | Ahn | |
| 2008/0004613 A1 * | 1/2008 | Barbut et al. | 606/21 |
| 2008/0077126 A1 * | 3/2008 | Rashidi | 606/34 |
| 2008/0147056 A1 * | 6/2008 | van der Weide et al. | 606/33 |
| 2008/0161890 A1 | 7/2008 | Lafontaine | |
| 2008/0269737 A1 * | 10/2008 | Elmouelhi | A61B 18/1477 606/41 |
| 2009/0082837 A1 * | 3/2009 | Gellman et al. | 607/105 |
| 2009/0088735 A1 * | 4/2009 | Abboud et al. | 606/22 |
| 2010/0234839 A1 | 9/2010 | Smith | |
| 2011/0021879 A1 | 1/2011 | Hart et al. | |
| 2012/0232549 A1 | 9/2012 | Willyard et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| EP | 1506757 | 2/2005 |
| EP | 1 707 126 A1 | 10/2006 |
| EP | 1905375 | 4/2008 |
| EP | 2098184 | 9/2009 |
| EP | 2158868 | 3/2010 |
| EP | 2255742 | 12/2010 |
| EP | 2322113 | 5/2011 |
| EP | 2399646 | 12/2011 |
| EP | 2 422 725 A2 | 2/2012 |
| EP | 2 462 883 A1 | 6/2012 |
| FR | 179 607 | 11/1906 |
| FR | 1 275 415 | 10/1961 |
| FR | 1 347 865 | 11/1963 |

(56) References Cited

FOREIGN PATENT DOCUMENTS

| | | |
|---|---|---|
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | S62125604 A | 6/1987 |
| JP | H02299647 A | 12/1990 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | H08505544 A | 6/1996 |
| JP | 08252263 | 10/1996 |
| JP | 09000492 | 1/1997 |
| JP | 09010223 | 1/1997 |
| JP | H11504539 A | 4/1999 |
| JP | 11244298 | 9/1999 |
| JP | 2000502585 A | 3/2000 |
| JP | 2000342599 | 12/2000 |
| JP | 2000350732 | 12/2000 |
| JP | 2001008944 | 1/2001 |
| JP | 2001-5014911 T | 2/2001 |
| JP | 2001029356 | 2/2001 |
| JP | 2001501491 A | 2/2001 |
| JP | 2001128990 | 5/2001 |
| JP | 2006187668 A | 7/2006 |
| JP | 2006314785 A | 11/2006 |
| JP | 2007195981 A | 8/2007 |
| JP | 2008142467 | 6/2008 |
| JP | 2008520382 A | 6/2008 |
| JP | 2001231870 | 8/2008 |
| JP | 2009207898 A | 9/2009 |
| JP | 2010-512892 T | 4/2010 |
| JP | 2010512892 A | 4/2010 |
| SU | 166452 | 11/1964 |
| SU | 401367 | 11/1974 |
| SU | 727201 | 4/1980 |
| WO | WO99/53853 | 10/1999 |
| WO | 0036985 | 6/2000 |
| WO | WO00/053113 | 9/2000 |
| WO | 2007/006158 | 1/2007 |
| WO | WO2010/035831 | 4/2010 |
| WO | WO 2010/042913 A2 | 4/2010 |
| WO | 2011/063061 | 5/2011 |

OTHER PUBLICATIONS

European Search Report for European Application No. 11010093.0 dated Mar. 20, 2012.
European Search Report for European Application No. 11010176.3 dated Mar. 19, 2012.
European Search Report for European Application No. 11010177.1 dated May 2, 2012.
European Search Report for European Application No. 11010175.5 dated Apr. 26, 2012.
Extended European Search Report dated Mar. 6, 2014 for EP 13 00 4371.
Partial European Search Report dated Jan. 14, 2014 for EP 12 15 4733.
Australian Office Action for Australian Appln. No. AU 2014206157 dated Oct. 20, 2015.
Japanese Office Action and Translation for JP 2012-052613 dated Nov. 17, 2015.
Japanese Office Action for JP 2012-052613 dated May 31, 2016.
Canadian Office Action dated May 28, 2018 for Canadian Appln. No. 2,770,810.
Final Rejection issued in Japanese Appl. No. 2017-066845, dated Jul. 24, 2018, together with English language translation (7 pages).

U.S. Appl. No. 08/136,098, filed Oct. 14, 1993, Roger A. Stern.
U.S. Appl. No. 08/483,742, filed Jun. 7, 1995, Roger A. Stern
U.S. Appl. No. 12/619,323, filed Nov. 16, 2009, Arnold V. DeCarlo.
U.S. Appl. No. 12/619,462, filed Nov. 11, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/722,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.

(56) References Cited

OTHER PUBLICATIONS

Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds In Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure# Vessel Sealing System: A Case Report" Innovations That Work, Feb. 2002.
Humphries Jr. et al., "Finite•Element Codes To Model Electrical Heating And Non•LInear Thermal Transport In Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Intl Federation of Gynecology and Obstetrics FIGO World Congress 2000, Washington, DC.

(56) References Cited

OTHER PUBLICATIONS

MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure# Atlas 20 cm Open Instrument" Innovations That Work, Jun. 2003.
Muller et al., "Extended Left Hemicolectomy Using the LigaSure ™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et aI., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.

(56) References Cited

OTHER PUBLICATIONS

European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.

(56) References Cited

OTHER PUBLICATIONS

International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.

* cited by examiner

SYSTEMS FOR THERMAL-FEEDBACK-CONTROLLED RATE OF FLUID FLOW TO FLUID-COOLED ANTENNA ASSEMBLY AND METHODS OF DIRECTING ENERGY TO TISSUE USING SAME

BACKGROUND

1. Technical Field

The present disclosure relates to electrosurgical devices and, more particularly, to systems for thermal-feedback-controlled rate of fluid flow to a fluid-cooled antenna assembly and methods of directing energy to tissue using the same.

2. Discussion of Related Art

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator that functions as an energy source, and a microwave surgical instrument (e.g., microwave ablation probe) having an antenna assembly for directing the energy to the target tissue. The microwave generator and surgical instrument are typically operatively-coupled by a cable assembly having a plurality of conductors for transmitting microwave energy from the generator to the instrument, and for communicating control, feedback and identification signals between the instrument and the generator.

There are several types of microwave probes in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor that can be formed in various configurations. The main modes of operation of a helical antenna assembly are normal mode (broadside), in which the field radiated by the helix is maximum in a perpendicular plane to the helix axis, and axial mode (end fire), in which maximum radiation is along the helix axis.

A microwave transmission line typically includes a thin inner conductor that extends along the longitudinal axis of the transmission line and is surrounded by a dielectric material and is further surrounded by an outer conductor around the dielectric material such that the outer conductor also extends along the transmission line axis. In one variation of an antenna, a waveguiding structure, such as a length of transmission line or coaxial cable, is provided with a plurality of openings through which energy "leaks" or radiates away from the guiding structure. This type of construction is typically referred to as a "leaky coaxial" or "leaky wave" antenna.

Because of the small temperature difference between the temperature required for denaturing malignant cells and the temperature normally injurious to healthy cells, a known heating pattern and precise temperature control is needed to lead to more predictable temperature distribution to eradicate the tumor cells while minimizing the damage to surrounding normal tissue. Excessive temperatures can cause adverse tissue effects. During the course of heating, tissue in an overly-heated area may become desiccated and charred. As tissue temperature increases to 100° C., tissue will lose water content due to evaporation or by the diffusion of liquid water from treated cells, and the tissue becomes desiccated. This desiccation of the tissue changes the electrical and other material properties of the tissue, and may impede treatment. For example, as the tissue is desiccated, the electrical resistance of the tissue increases, making it increasingly more difficult to supply power to the tissue. Desiccated tissue may also adhere to the device, hindering delivery of power. At tissue temperatures in excess of 100° C., the solid contents of the tissue begin to char. Like desiccated tissue, charred tissue is relatively high in resistance to current and may impede treatment.

Microwave ablation probes may utilize fluid circulation to cool thermally-active components and dielectrically load the antenna radiating section. During operation of a microwave ablation device, if proper cooling is not maintained, e.g., flow of coolant fluid is interrupted or otherwise insufficient to cool device components sensitive to thermal failure, the ablation device may be susceptible to rapid failures due to the heat generated from the increased reflected power. In such cases, the time to failure is dependent on the power delivered to the antenna assembly and the duration and degree to which coolant flow is reduced or interrupted.

Cooling the ablation probe may enhance the overall heating pattern of the antenna, prevent damage to the antenna and prevent harm to the clinician or patient. During some procedures, the amount of cooling may not be sufficient to prevent excessive heating and resultant adverse tissue effects. Some systems for cooling an ablation device may allow the ablation device to be over-cooled, such as when the device is operating at low power settings. Over-cooling may prevent proper treatment or otherwise impede device tissue effect by removing thermal energy from the targeted ablation site.

SUMMARY

The present disclosure relates to an electrosurgical system including an electrosurgical device adapted to direct energy to tissue, one or more temperature sensors associated with the electrosurgical device, a fluid-flow path leading to the electrosurgical device, and a flow-control device disposed in fluid communication with the fluid-flow path. The system also includes a processor unit communicatively-coupled to the one or more temperature sensors and communicatively-coupled to the flow-control device. The processor unit is configured to control the flow-control device based on determination of a desired fluid-flow rate using one or more electrical signals outputted from the one or more temperature sensors.

The present disclosure also relates to an electrosurgical system including an electrosurgical device adapted to direct energy to tissue and a coolant supply system adapted to provide coolant fluid to the electrosurgical device. The coolant supply system includes a coolant source, a first fluid-flow path fluidly-coupled to the electrosurgical device to provide fluid flow from the coolant source to the electrosurgical device, a second fluid-flow path fluidly-coupled to the electrosurgical device to provide fluid flow from the energy applicator to the coolant source, a third fluid-flow path fluidly-coupled to the first fluid-flow path and the second fluid-flow path, and a flow-control device disposed in fluid communication with the third fluid-flow path. The system also includes one or more temperature sensors associated with the electrosurgical device and a feedback control system adapted to provide a thermal-feedback-controlled rate of fluid flow to the electrosurgical device. The feedback control system includes a processor unit communicatively-coupled to the one or more temperature sensors and communicatively-coupled to the flow-control device. The processor unit is configured to control the flow-control device based on determination of a desired fluid-flow rate using one or more electrical signals outputted from the one or more temperature sensors.

The present disclosure also relates to a method of directing energy to tissue using a fluid-cooled antenna assembly including the initial step of providing an energy applicator. The energy applicator includes an antenna assembly and a hub providing at least one coolant connection to the energy applicator. The method also includes the steps of providing a coolant supply system including a fluid-flow path fluidly-coupled to the hub for providing fluid flow to the energy applicator, positioning the energy applicator in tissue for the delivery of energy to tissue when the antenna assembly is energized, and providing a thermal-feedback-controlled rate of fluid flow to the antenna assembly when energized using a feedback control system operably-coupled to a flow-control device disposed in fluid communication with the fluid-flow path.

The present disclosure also relates to a method of directing energy to tissue using a fluid-cooled antenna assembly including the initial steps of providing an energy applicator and a coolant supply system adapted to provide coolant fluid to the energy applicator. The energy applicator includes an antenna assembly and a coolant chamber adapted to circulate coolant fluid around at least a portion of the antenna assembly. The coolant chamber is fluidly-coupled to the coolant supply system. The method also includes the steps of positioning the energy applicator in tissue for the delivery of energy to tissue when the antenna assembly is energized, and providing a thermal-feedback-controlled rate of fluid flow to the antenna assembly when energized by using a feedback control system including a processor unit configured to control a flow-control device associated with the coolant supply system based on determination of a desired fluid-flow rate using one or more electrical signals outputted from one or more temperature sensors associated with the energy applicator.

BRIEF DESCRIPTION OF THE DRAWINGS

Objects and features of the presently-disclosed systems for thermal-feedback-controlled rate of fluid flow to a fluid-cooled antenna assembly and methods of directing energy to tissue using the same will become apparent to those of ordinary skill in the art when descriptions of various embodiments thereof are read with reference to the accompanying drawings, of which.

DETAILED DESCRIPTION

Figure 1:
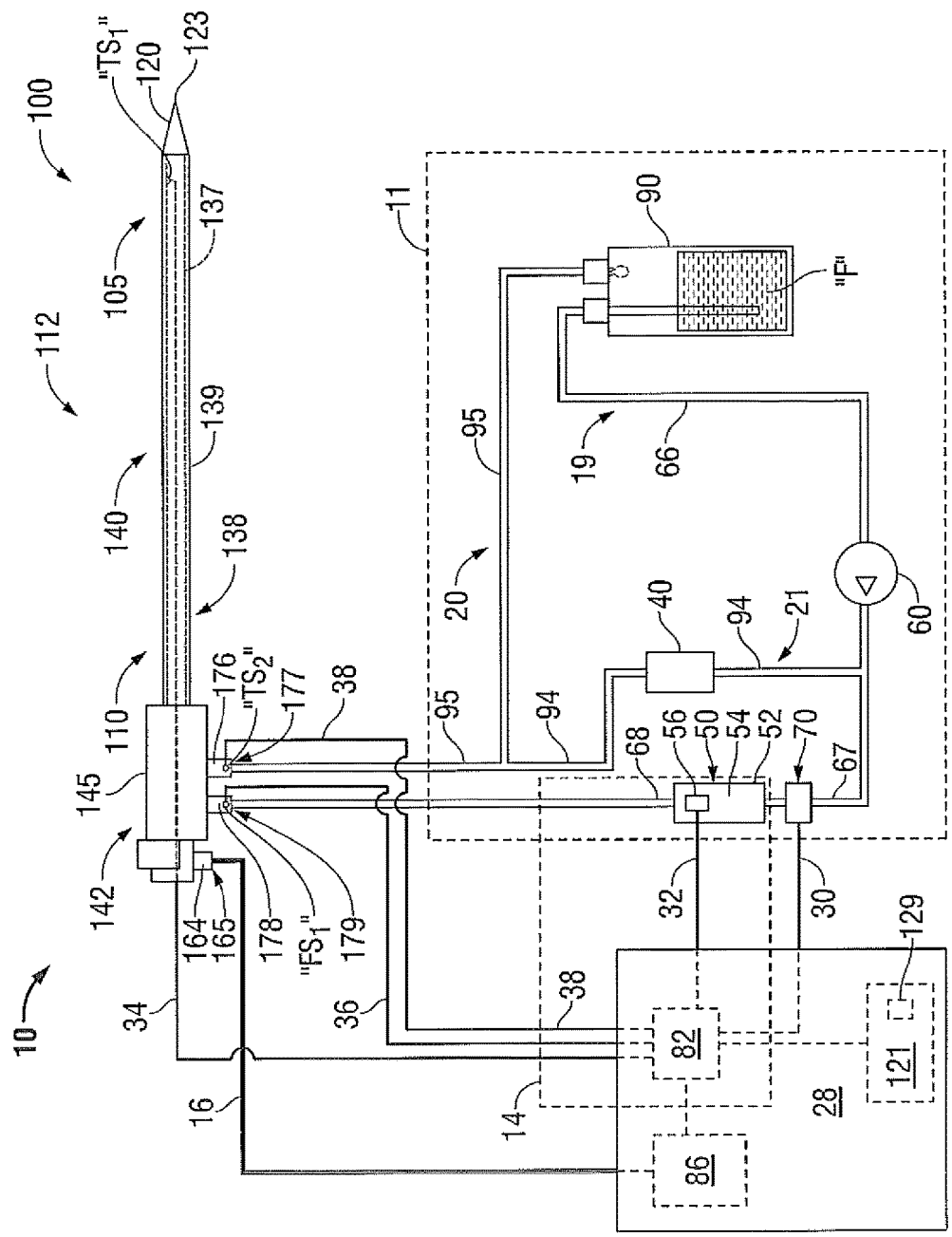
FIG. 1 is a schematic diagram of an electrosurgical system including an energy-delivery device and a feedback control system operably associated with a fluid supply system fluidly-coupled to the energy-delivery device in accordance with an embodiment of the present disclosure.

Hereinafter, embodiments of the presently-disclosed systems for thermal-feedback-controlled rate of fluid flow to a fluid-cooled antenna assembly and methods of directing energy to tissue using the same are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second).

As it is used in this description, "ablation procedure" generally refers to any ablation procedure, such as, for example, microwave ablation, radiofrequency (RF) ablation, or microwave or RF ablation-assisted resection. As it is used in this description, "energy applicator" generally refers to any device that can be used to transfer energy from a power generating source, such as a microwave or RF electrosurgical generator, to tissue. For the purposes herein, the term "energy-delivery device" is interchangeable with the term "energy applicator". As it is used in this description, "transmission line" generally refers to any transmission medium that can be used for the propagation of signals from one point to another.

As it is used in this description, "fluid" generally refers to a liquid, a gas, a liquid containing a dissolved gas or dissolved gases, a mixture of gas and liquid, gas and suspended solids, liquid and suspended solids, or a mixture of gas, liquid and suspended solids. As it is used in this description, "rate of fluid flow" generally refers to volumetric flow rate. Volumetric flow rate may be defined as a measure of the volume of fluid passing a point in a system per unit time, e.g., cubic meters per second ($m^3 \ s^{-1}$) in SI units, or cubic feet per second (Cu ft/s). Generally speaking, volumetric fluid-flow rate can be calculated as the product of the cross-sectional area for flow and the flow velocity. In the context of mechanical valves, the fluid-flow rate, in the given through-flow direction, may be considered to be a function of the variable restriction geometry for a given flow passage configuration and pressure drop across the restriction. For the purposes herein, the term "fluid-flow rate" is interchangeable with the term "rate of fluid flow".

As it is used in this description, "pressure sensor" generally refers to any pressure-sensing device capable of generating a signal representative of a pressure value. For the purposes herein, the term "pressure transducer" is interchangeable with the term "pressure sensor".

As it is used herein, the term "computer" generally refers to anything that transforms information in a purposeful way. For the purposes of this description, the terms "software" and "code" should be interpreted as being applicable to software, firmware, or a combination of software and firmware. For the purposes of this description, "non-transitory" computer-readable media include all computer-readable media, with the sole exception being a transitory, propagating signal.

Various embodiments of the present disclosure provide systems for thermal-feedback-controlled rate of fluid flow to an electrosurgical device, such as an ablation probe including a fluid-cooled antenna assembly. Embodiments may be implemented using electromagnetic radiation at microwave frequencies or at other frequencies. An electrosurgical system including a coolant supply system and a feedback control system adapted to provide a thermal-feedback-controlled rate of fluid flow to an energy applicator, according to various embodiments, is designed and configured to operate between about 300 MHz and about 10 GHz. Systems for thermal-feedback-controlled rate of fluid flow to electrosurgical devices, as described herein, may be used in conjunction with various types of devices, such as microwave antenna assemblies having either a straight or looped radiating antenna portion, etc., which may be inserted into or placed adjacent to tissue to be treated.

Various embodiments of the presently-disclosed electrosurgical systems including a feedback control system adapted to provide a thermal-feedback-controlled rate of fluid flow to an energy applicator disposed in fluid communication with a coolant supply system are suitable for microwave ablation and for use to pre-coagulate tissue for microwave ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, although the following description describes the use of a dipole microwave antenna, the teachings of the present disclosure may also apply to a monopole, helical, or other suitable type of antenna assembly.

FIG. 1 shows an electrosurgical system 10 according to an embodiment of the present disclosure that includes an energy applicator or probe 100, an electrosurgical power generating source 28, e.g., a microwave or RF electrosurgical generator, and a feedback control system 14 operably associated with a coolant supply system 11. Probe 100 is operably-coupled to the electrosurgical power generating source 28, and disposed in fluid communication with the coolant supply system 11. In some embodiments, one or more components of the coolant supply system 11 may be integrated fully or partially into the electrosurgical power generating source 28. Coolant supply system 11, which is described in more detail later in this description, is adapted to provide coolant fluid "F" to the probe 100. Probe 100, which is described in more detail later in this description, may be integrally associated with a hub 142 configured to provide electrical and/or coolant connections to the probe. In some embodiments, the probe 100 may extend from a handle assembly (not shown).

In some embodiments, the electrosurgical system 10 includes one or more sensors capable of generating a signal indicative of a temperature of a medium in contact therewith (referred to herein as temperature sensors) and/or one or more sensors capable of generating a signal indicative of a rate of fluid flow (referred to herein as flow sensors). In such embodiments, the feedback control system 14 may be adapted to provide a thermal-feedback-controlled rate of fluid flow to the probe 100 using one or more signals output from one or more temperature sensors and/or one or more flow sensors operably associated with the probe 100 and/or conduit fluidly-coupled to the probe 100.

Figure 2:
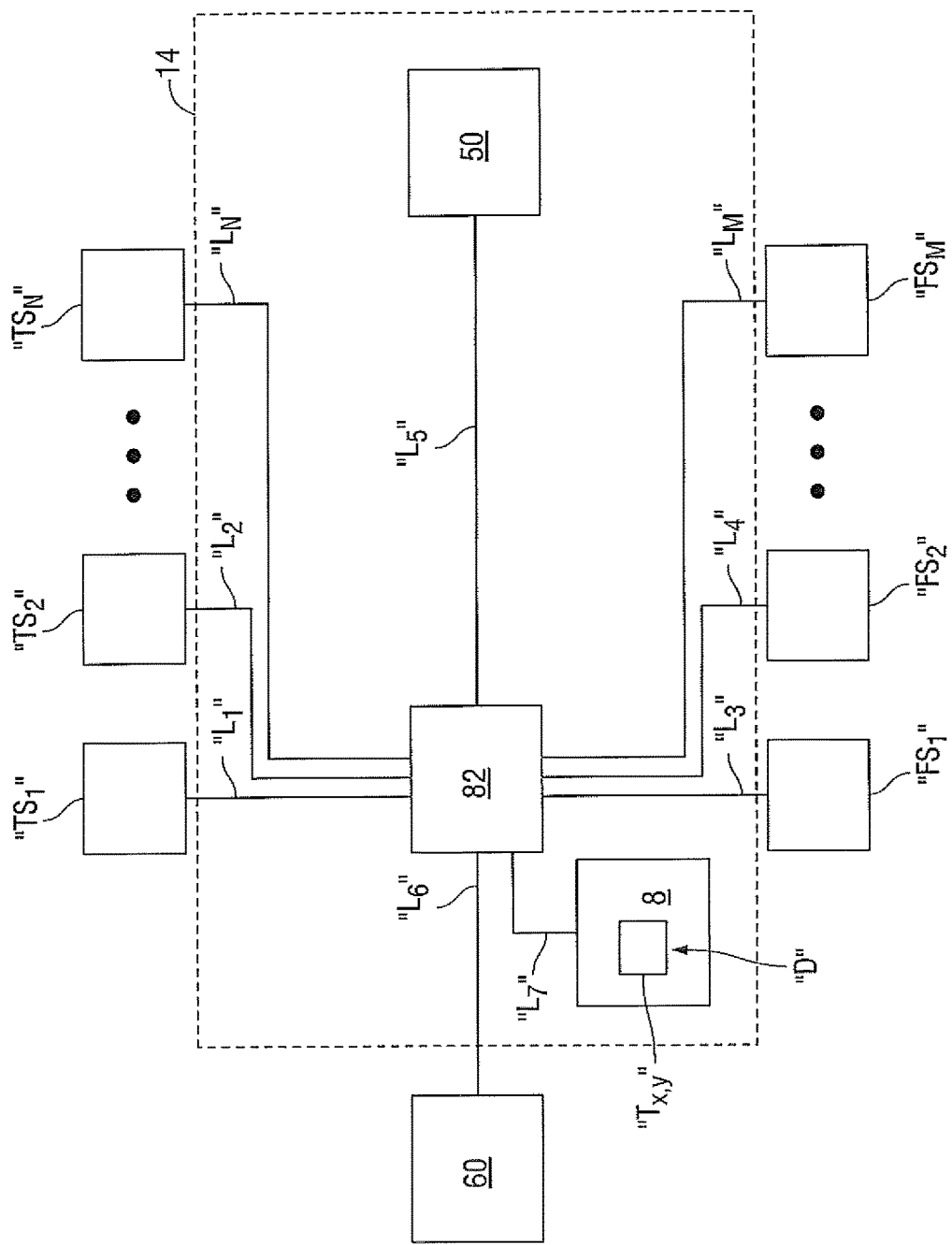
FIG. 2 is a schematic diagram of a feedback control system, such as the feedback control system of FIG. 1, in accordance with an embodiment of the present disclosure.

An embodiment of a feedback control system, such as the feedback control system 14 of FIG. 1, in accordance with the present disclosure, is shown in more detail in FIG. 2. It is to be understood, however, that other feedback control system embodiments (e.g., feedback control systems 414 and 514 shown in FIGS. 4 and 5, respectively) may be used in conjunction with coolant supply systems in various configurations. In some embodiments, the feedback control system 14, or component(s) thereof, may be integrated fully or partially into the electrosurgical power generating source 28.

In the embodiment shown in FIG. 1, the feedback control system 14 is operably associated with a processor unit 82 disposed within or otherwise associated with the electrosurgical power generating source 28. Processor unit 82 may be communicatively-coupled to one or more components or modules of the electrosurgical power generating source 28, e.g., a user interface 121 and a generator module 86. Processor unit 82 may additionally, or alternatively, be communicatively-coupled to one or more temperature sensors (e.g., two sensors "$TS_1$" and "$TS_2$" shown in FIG. 1) and/or one or more flow sensors (e.g., one sensor "$FS_1$" shown in FIG. 1) for receiving one or more signals indicative of a temperature (referred to herein as temperature data) and/or one or more signals indicative of a flow rate (referred to herein as flow data). Transmission lines may be provided to electrically couple the temperature sensors, flow sensors and/or other sensors, e.g., pressure sensors, to the processor unit 82.

Feedback control system embodiments may additionally, or alternatively, be operably associated with a processor unit deployed in a standalone configuration, and/or a processor unit disposed within the probe 100 or otherwise associated therewith. In some embodiments, where the probe 100 extends from a handle assembly (not shown), the feedback control system may be operably associated with a processor unit disposed within the handle assembly. Examples of handle assembly embodiments are disclosed in commonly assigned U.S. patent application Ser. No. 12/686,726 filed on Jan. 13, 2010, entitled "ABLATION DEVICE WITH USER INTERFACE AT DEVICE HANDLE, SYSTEM INCLUDING SAME, AND METHOD OF ABLATING TISSUE USING SAME".

Electrosurgical power generating source 28 may include any generator suitable for use with electrosurgical devices, and may be configured to provide various frequencies of electromagnetic energy. In some embodiments, the electrosurgical power generating source 28 is configured to provide microwave energy at an operational frequency from about 300 MHz to about 10 GHz. In some embodiments, the electrosurgical power generating source 28 is configured to provide electrosurgical energy at an operational frequency from about 400 KHz to about 500 KHz. An embodiment of an electrosurgical power generating source, such as the electrosurgical power generating source 28 of FIG. 1, in accordance with the present disclosure, is shown in more detail in FIG. 3.

Probe 100 may include one or more antennas of any suitable type, such as an antenna assembly (or antenna array) suitable for use in tissue ablation applications. For ease of explanation and understanding, the probe 100 is described as including a single antenna assembly 112. In some embodiments, the antenna assembly 112 is substantially disposed within a sheath 138. Probe 100 generally includes a coolant chamber 137 defined about the antenna assembly 112. In some embodiments, the coolant chamber 137, which is described in more detail later in this description, includes an interior lumen defined by the sheath 138.

Probe 100 may include a feedline 110 coupled to the antenna assembly 112. A transmission line 16 may be provided to electrically couple the feedline 110 to the electrosurgical power generating source 28. Feedline 110 may be coupled to a connection hub 142, which is described in more detail later in this description, to facilitate the flow of coolant and/or buffering fluid into, and out of, the probe 100.

In the embodiment shown in FIG. 1, the feedback control system 14 is operably associated with a flow-control device 50 disposed in fluid communication with a fluid-flow path of the coolant supply system 11 (e.g., first coolant path 19) fluidly-coupled to the probe 100. Flow-control device 50 may include any suitable device capable of regulating or controlling the rate of fluid flow passing though the flow-control device 50, e.g., a valve of any suitable type operable to selectively impede or restrict flow of fluid through passages in the valve. Processor unit 82 may be configured to control the flow-control device 50 based on determination of a desired fluid-flow rate using temperature data received from one or more temperature sensors (e.g., "TS$_1$", "TS$_2$" through "TS$_N$" shown in FIG. 2).

In some embodiments, the flow-control device 50 includes a valve 52 including a valve body 54 and an electromechanical actuator 56 operatively-coupled to the valve body 54. Valve body 54 may be implemented as a ball valve, gate valve, butterfly valve, plug valve, or any other suitable type of valve. In the embodiment shown in FIG. 1, the actuator 56 is communicatively-coupled to the processor unit 82 via a transmission line 32. Processor unit 82 may be configured to control the flow-control device 50 by activating the actuator 56 to selectively adjust the fluid-flow rate in a fluid-flow path (e.g., first coolant path 19 of the coolant supply system 11) fluidly-coupled to the connection hub 142 to achieve a desired fluid-flow rate. The desired fluid-flow rate may be determined by a computer program and/or logic circuitry associated with the processor unit 82. The desired fluid-flow rate may additionally, or alternatively, be selected from a look-up table "T$_{X,Y}$" (shown in FIGS. 2 and 5) or determined by a computer algorithm stored within a memory device 8 (shown in FIGS. 2 and 5).

Embodiments including a suitable pressure-relief device 40 disposed in fluid communication with the diversion flow path 21 may allow the fluid-movement device 60 to run at a substantially constant speed and/or under a near-constant load (head pressure) regardless of the selective adjustment of the fluid-flow rate in the first coolant path 19. Utilizing a suitable pressure-relief device 40 disposed in fluid communication with the diversion flow path 21, in accordance with the present disclosure, may allow the fluid-movement device 60 to be implemented as a single speed device, e.g., a single speed pump.

Feedback control system 14 may utilize data "D" (e.g., data representative of a mapping of temperature data to settings for properly adjusting one or more operational parameters of the flow-control device 50 to achieve a desired temperature and/or a desired ablation) stored in a look-up table "T$_{X,Y}$" (shown in FIGS. 2 and 5), where X denotes columns and Y denotes rows, or other data structure, to determine the desired fluid-flow rate. In the embodiment shown in FIG. 1, the electrosurgical system 10 includes a first temperature sensor "TS$_1$" capable of generating a signal indicative of a temperature of a medium in contact therewith and a second temperature sensor "TS$_2$" capable of generating a signal indicative of a temperature of a medium in contact therewith. Feedback control system 14 may be configured to utilize signals received from the first temperature sensor "TS$_1$" and/or the second temperature sensor "TS$_2$" to control the flow-control device 50.

In some embodiments, the electrosurgical system 10 includes a flow sensor "FS$_1$" communicatively-coupled to the processor unit 82, e.g., via a transmission line 36. In some embodiments, the flow sensor "FS$_1$" may be disposed in fluid communication with the first coolant path 19 or the second coolant path 20. Processor unit 82 may be configured to control the flow-control device 50 based on determination of a desired fluid-flow rate using one or more signals received from the flow sensor "FS$_1$". In some embodiments, the processor unit 82 may be configured to control the flow-control device 50 based on determination of a desired fluid-flow rate using one or more signals received from the flow sensor "FS$_1$" in conjunction with one or more signals received from the first temperature sensor "TS$_1$" and/or the second temperature sensor "TS$_2$". Although the electrosurgical system 10 shown in FIG. 1 includes one flow sensor "FS$_1$", alternative embodiments may be implemented with a plurality of flow sensors (e.g., "FS$_1$", "FS$_2$" through "FS$_M$" shown in FIG. 2) adapted to provide a measurement of the rate of fluid flow into and/or out of the probe 100 and/or conduit fluidly-coupled to the probe 100.

Electrosurgical system 10 may additionally, or alternatively, include one or more pressure sensors (e.g., "PS$_1$", "PS$_2$" through "PS$_K$" shown in FIG. 5) adapted to provide a measurement of the fluid pressure in the probe 100 and/or conduit fluidly-coupled to the probe 100. In some embodiments, the electrosurgical system 10 includes one or more pressure sensors (e.g., pressure sensor 70) disposed in fluid communication with one or more fluid-flow paths (e.g., first coolant path 19) of the coolant supply system 11 as opposed to a pressure sensor disposed within the probe 100, reducing cost and complexity of the probe 100.

In the embodiment shown in FIG. 1, the processor unit 82 is operably associated with a pressure sensor 70 disposed in fluid communication with a fluid-flow path of the coolant supply system 11. Processor unit 82 may be communicatively-coupled to the pressure sensor 70 via a transmission line 30 or wireless link. Processor unit 82 may additionally, or alternatively, be operably associated with one or more pressure sensors disposed within the probe 100, e.g., disposed in fluid communication with the coolant chamber 137.

Pressure sensor 70 may include any suitable type of pressure sensor, pressure transducer, pressure transmitter, or pressure switch. Pressure sensor 70 (also referred to herein as "pressure transducer") may include a variety of components, e.g., resistive elements, capacitive elements and/or piezo-resistive elements, and may be disposed at any suitable position in the coolant supply system 11. In some embodiments, the pressure transducer 70 is disposed in fluid communication with the first coolant path 19 located between the fluid-movement device 60 and the flow-control device 50, e.g., placed at or near the flow-control device 50.

In some embodiments, the processor unit 82 may be configured to control the flow-control device 50 based on determination of a desired fluid-flow rate using pressure data received from one or more pressure sensors. In some embodiments, the processor unit 82 may be configured to control the flow-control device 50 based on determination of a desired fluid-flow rate using one or more signals received from the first temperature sensor "TS$_1$" and/or the second temperature sensor "TS$_2$" and/or the flow sensor "FS$_1$" in conjunction with one or more signals received from the pressure transducer 70.

In some embodiments, the processor unit 82 may be configured to control the amount of power delivered to the antenna assembly 112 based on time and power settings provided by the user in conjunction with sensed temperature signals indicative of a temperature of a medium, e.g., coolant fluid "F", in contact with one or one temperature sensors operably associated with the antenna assembly 112 and/or the connection hub 142. In some embodiments, the processor unit 82 may be configured to decrease the amount of power delivered to the antenna assembly 112 when sensed temperature signals indicative of a temperature below a predetermined temperature threshold are received by processor unit 82, e.g., over a predetermined time interval.

Processor unit 82 may be configured to control one or more operating parameters associated with the electrosurgical power generating source 28 based on determination of whether the pressure level of fluid in the probe 100 and/or conduit fluidly-coupled to the probe 100 is above a predetermined threshold using pressure data received from one or more pressure sensors, e.g., pressure transducer 70. Examples of operating parameters associated with the electrosurgical power generating source 28 include without limitation temperature, impedance, power, current, voltage, mode of operation, and duration of application of electromagnetic energy.

In some embodiments, the output signal of the pressure transducer 70, representing a pressure value and possibly amplified and/or conditioned by means of suitable components (not shown), is received by the processor unit 82 and used for determination of whether the pressure level of fluid in the probe 100 and/or conduit fluidly-coupled to the probe 100 is above a predetermined threshold in order to control when power is delivered to the antenna assembly 112. In some embodiments, in response to a determination that the pressure level of fluid in the probe 100 and/or conduit fluidly-coupled to the probe 100 is below the predetermined threshold, the processor unit 82 may be configured to decrease the amount of power delivered to the antenna assembly 112 and/or to stop energy delivery between the electrosurgical power generating source 28 and the probe 100. In some embodiments, the processor unit 82 may be configured to enable energy delivery between the electrosurgical power generating source 28 and the probe 100 based on determination that the pressure level of fluid in the probe 100 and/or conduit fluidly-coupled to the probe 100 is above the predetermined threshold.

In some embodiments, the pressure transducer 70 is adapted to output a predetermined signal to indicate a sensed pressure below that of the burst pressure of the pressure-relief device 40. A computer program and/or logic circuitry associated with the processor unit 82 may be configured to enable the electrosurgical power generating source 28 and the flow-control device 50 in response to a signal from the pressure transducer 70. A computer program and/or logic circuitry associated with the processor unit 82 may be configured to output a signal indicative of an error code and/or to activate an indicator unit 129 if a certain amount of time elapses between the point at which energy delivery to the probe 100 is enabled and when the pressure signal is detected, e.g., to ensure that the fluid-movement device 60 is turned on and/or that the probe 100 is receiving flow of fluid before the antenna assembly 112 can be activated.

As shown in FIG. 1, a feedline 110 couples the antenna assembly 112 to a connection hub 142. Connection hub 142 may have a variety of suitable shapes, e.g., cylindrical, rectangular, etc. Connection hub 142 generally includes a hub body 145 defining an outlet fluid port 177 and an inlet fluid port 179. Hub body 145 may include one or more branches, e.g., three branches 164, 178 and 176, extending from one or more portions of the hub body 145. In some embodiments, one or more branches extending from the hub body 145 may be configured to house one or more connectors and/or ports, e.g., to facilitate the flow of coolant and/or buffering fluid into, and out of, the connection hub 142.

In the embodiment shown in FIG. 1, the hub body 145 includes a first branch 164 adapted to house a cable connector 165, a second branch 178 adapted to house the inlet fluid port 179, and a third branch 176 adapted to house the outlet fluid port 177. It is to be understood, however, that other connection hub embodiments may also be used. Examples of hub embodiments are disclosed in commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS".

In some embodiments, the flow sensor "FS$_1$" is disposed in fluid communication with the first coolant path 19, e.g., disposed within the inlet fluid port 179 or otherwise associated with the second branch 178, and the second temperature sensor "TS$_2$" is disposed in fluid communication with the second coolant path 20, e.g., disposed within the outlet fluid port 177 or otherwise associated with the third branch 176. In other embodiments, the second temperature sensor "TS₂" may be disposed within the inlet fluid port 179 or otherwise associated with the second branch 178, and the flow sensor "FS₁" may be disposed within the outlet fluid port 177 or otherwise associated with the third branch 176.

Coolant supply system 11 generally includes a substantially closed loop having a first coolant path 19 leading to the probe 100 and a second coolant path 20 leading from the probe 100, a coolant source 90, and a fluid-movement device 60, e.g., disposed in fluid communication with the first coolant path 19. In some embodiments, the coolant supply system 11 includes a third coolant path 21 (also referred to herein as a "diversion flow path") disposed in fluid communication with the first coolant path 19 and the second coolant path 20. The conduit layouts of the first coolant path 19, second coolant path 20 and third coolant path 21 may be varied from the configuration depicted in FIG. 1.

In some embodiments, a pressure-relief device 40 may be disposed in fluid communication with the diversion flow path 21. Pressure-relief device 40 may include any type of device, e.g., a spring-loaded pressure-relief valve, adapted to open at a predetermined set pressure and to flow a rated capacity at a specified over-pressure. In some embodiments, one or more flow-restrictor devices (not shown) suitable for preventing backflow of fluid into the first coolant path 19 may be disposed in fluid communication with the diversion flow path 21. Flow-restrictor devices may include a check valve or any other suitable type of unidirectional flow restrictor or backflow preventer, and may be disposed at any suitable position in the diversion flow path 21 to prevent backflow of fluid from the diversion flow path 21 into the first coolant path 19.

In some embodiments, the first coolant path 19 includes a first coolant supply line 66 leading from the coolant source 90 to the fluid-movement device 60, a second coolant supply line 67 leading from the fluid-movement device 60 to the flow-control device 50, and a third coolant supply line 68 leading from the flow-control device 50 to the inlet fluid port 179 defined in the second branch 178 of the connection hub body 145, and the second coolant path 20 includes a first coolant return line 95 leading from the outlet fluid port 177 defined in the third branch 176 of the hub body 145 to the coolant source 90. Embodiments including the diversion flow path 21 may include a second coolant return line 94 fluidly-coupled to the second coolant supply line 67 and the first coolant return line 95. Pressure-relief device 40 may be disposed at any suitable position in the second coolant return line 94. The spacing and relative dimensions of coolant supply lines and coolant return lines may be varied from the configuration depicted in FIG. 1.

Coolant source 90 may be any suitable housing containing a reservoir of coolant fluid "F". Coolant fluid "F" may be any suitable fluid that can be used for cooling or buffering the probe 100, e.g., deionized water, or other suitable cooling medium. Coolant fluid "F" may have dielectric properties and may provide dielectric impedance buffering for the antenna assembly 112. Coolant fluid "F" may be a conductive fluid, such as a saline solution, which may be delivered to the target tissue, e.g., to decrease impedance and allow increased power to be delivered to the target tissue. A coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. In other variations, gases (such as nitrous oxide, nitrogen, carbon dioxide, etc.) may also be utilized as the cooling fluid. In yet another variation, a combination of liquids and/or gases, including, for example, those mentioned above, may be utilized as the coolant fluid "F".

In the embodiment shown in FIG. 1, the fluid-movement device 60 is provided in the first coolant path 19 to move the coolant fluid "F" through the first coolant path 19 and into, and out of, the probe 100. Fluid-movement device 60 may include valves, pumps, power units, actuators, fittings, manifolds, etc. The position of the fluid-movement device 60, e.g., in relation to the coolant source 90, may be varied from the configuration depicted in FIG. 1. Although the coolant supply system 11 shown in FIG. 1 includes a single, fluid-movement device 60 located in the first coolant path 19, various combinations of different numbers of fluid-movement devices, variedly-sized and variedly-spaced apart from each other, may be provided in the first coolant path 19 and/or the second coolant path 20.

In some embodiments, the probe 100 includes a feedline 110 that couples the antenna assembly 112 to a hub, e.g., connection hub 142, that provides electrical and/or coolant connections to the probe 100. Feedline 110 may be formed from a suitable flexible, semi-rigid or rigid microwave conductive cable. Feedline 110 may be constructed of a variety of electrically-conductive materials, e.g., copper, gold, or other conductive metals with similar conductivity values. Feedline 110 may be made of stainless steel, which generally offers the strength required to puncture tissue and/or skin.

In some variations, the antenna assembly 112 includes a distal radiating portion 105 and a proximal radiating portion 140. In some embodiments, a junction member (not shown), which is generally made of a dielectric material, couples the proximal radiating section 140 and the distal radiating section 105. In some embodiments, the distal and proximal radiating sections 105, 140 align at the junction member and are also supported by an inner conductor (not shown) that extends at least partially through the distal radiating section 105.

Antenna assembly 112 may be provided with an end cap or tapered portion 120, which may terminate in a sharp tip 123 to allow for insertion into tissue with minimal resistance. One example of a straight probe with a sharp tip that may be suitable for use as the energy applicator 100 is an EVIDENT™ microwave ablation probe offered by Covidien. The end cap or tapered portion 120 may include other shapes, such as, for example, a tip 123 that is rounded, flat, square, hexagonal, or cylindroconical. End cap or tapered portion 120 may be formed of a material having a high dielectric constant, and may be a trocar.

Sheath 138 generally includes an outer jacket 139 defining a lumen into which the antenna assembly 112, or portion thereof, may be positioned. In some embodiments, the sheath 138 is disposed over and encloses the feedline 110, the proximal radiating portion 140 and the distal radiating portion 105, and may at least partially enclose the end cap or tapered portion 120. The outer jacket 139 may be formed of any suitable material, such as, for example, polymeric or ceramic materials. The outer jacket 139 may be a water-cooled catheter formed of a material having low electrical conductivity.

In accordance with the embodiment shown in FIG. 1, a coolant chamber 137 is defined by the outer jacket 139 and the end cap or tapered portion 120. Coolant chamber 137 is disposed in fluid communication with the inlet fluid port 179 and the outlet fluid port 177 and adapted to circulate coolant fluid "F" therethrough, and may include baffles, multiple lumens, flow restricting devices, or other structures that may redirect, concentrate, or disperse flow depending on their shape. Examples of coolant chamber embodiments are disclosed in commonly assigned U.S. patent application Ser. No. 12/350,292 filed on Jan. 8, 2009, entitled "CHOKED DIELECTRIC LOADED TIP DIPOLE MICROWAVE ANTENNA", commonly assigned U.S. patent application Ser. No. 12/401,268 filed on Mar. 10, 2009, entitled "COOLED DIELECTRICALLY BUFFERED MICROWAVE DIPOLE ANTENNA", and U.S. Pat. No. 7,311,703, entitled "DEVICES AND METHODS FOR COOLING MICROWAVE ANTENNAS". The size and shape of the sheath 138 and the coolant chamber 137 extending therethrough may be varied from the configuration depicted in FIG. 1.

During microwave ablation, e.g., using the electrosurgical system 10, the probe 100 is inserted into or placed adjacent to tissue and microwave energy is supplied thereto. Ultrasound or computed tomography (CT) guidance may be used to accurately guide the probe 100 into the area of tissue to be treated. Probe 100 may be placed percutaneously or atop tissue, e.g., using conventional surgical techniques by surgical staff. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue. Single or multiple probes 100 may be used to provide ablations in short procedure times, e.g., a few seconds to minutes, to destroy cancerous cells in the target tissue region.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Tissue ablation size and geometry is influenced by a variety of factors, such as the energy applicator design, number of energy applicators used simultaneously, time and wattage.

In operation, microwave energy having a wavelength, lambda ($\lambda$), is transmitted through the antenna assembly 112, e.g., along the proximal and distal radiating portions 140, 105, and radiated into the surrounding medium, e.g., tissue. The length of the antenna for efficient radiation may be dependent on the effective wavelength $\lambda_{eff}$ which is dependent upon the dielectric properties of the medium being radiated. Antenna assembly 112, through which microwave energy is transmitted at a wavelength $\lambda$, may have differing effective wavelengths $\lambda_{eff}$ depending upon the surrounding medium, e.g., liver tissue as opposed to breast tissue.

In some embodiments, the electrosurgical system 10 includes a first temperature sensor "$TS_1$" disposed within a distal radiating portion 105 of the antenna assembly 112. First temperature sensor "$TS_1$" may be disposed within or contacting the end cap or tapered portion 120. It is to be understood that the first temperature sensor "$TS_1$" may be disposed at any suitable position to allow for the sensing of temperature. Processor unit 82 may be electrically connected by a transmission line 34 to the first temperature sensor "$TS_1$". Sensed temperature signals indicative of a temperature of a medium in contact with the first temperature sensor "$TS_1$" may be utilized by the processor unit 82 to control the flow of electrosurgical energy and/or the flow rate of coolant to attain the desired ablation.

Electrosurgical system 10 may additionally, or alternatively, include a second temperature sensor "$TS_2$" disposed within the outlet fluid port 177 or otherwise associated with the third branch 176 of the hub body 145. Processor unit 82 may be electrically connected by a transmission line 38 to the second temperature sensor "$TS_2$". First temperature sensor "$TS_1$" and/or the second temperature sensor "$TS_2$" may be a thermocouple, thermistor, or other temperature sensing device. A plurality of sensors may be utilized including units extending outside the tip 123 to measure temperatures at various locations in the proximity of the tip 123.

FIG. 2 schematically illustrates an embodiment of a feedback control system, such as the feedback control system 14 of FIG. 1, in accordance with the present disclosure, that includes the processor unit 82 and a memory device 8 in operable connection with the processor unit 82. In some embodiments, the memory device 8 may be associated with the electrosurgical power generating source 28. In some embodiments, the memory device 8 may be implemented as a storage device 88 (shown in FIG. 3) integrated into the electrosurgical power generating source 28. In some embodiments, the memory device 8 may be implemented as an external device 81 (shown in FIG. 3) communicatively-coupled to the electrosurgical power generating source 28.

In some embodiments, the processor unit 82 is communicatively-coupled to the flow-control device 50, e.g., via a transmission line "$L_5$", and may be communicatively-coupled to the fluid-movement device 60, e.g., via a transmission line "$L_6$". In some embodiments, the processor unit 82 may be configured to control one or more operational parameters of the fluid-movement device 60 to selectively adjust the fluid-flow rate in a fluid-flow path (e.g., first coolant path 19) of the coolant supply system 11. In one non-limiting example, the fluid-movement device 60 is implemented as a multi-speed pump, and the processor unit 82 may be configured to vary the pump speed to selectively adjust the fluid-flow rate to attain a desired fluid-flow rate.

Processor unit 82 may be configured to execute a series of instructions to control one or more operational parameters of the flow-control device 50 based on determination of a desired fluid-flow rate using temperature data received from one or more temperature sensors, e.g., "$TS_1$", "$TS_2$" through "$TS_N$", where N is an integer. The temperature data may be transmitted via transmission lines "$L_1$", "$L_2$" through "$L_N$" or wirelessly transmitted. One or more flow sensors, e.g., "$FS_1$", "$FS_2$" through "$FS_M$", where M is an integer, may additionally, or alternatively, be communicatively-coupled to the processor unit 82, e.g., via transmission lines "$L_3$", "$L_4$" through "$L_M$". In some embodiments, signals indicative of the rate of fluid flow into and/or out of the probe 100 and/or conduit fluidly-coupled to the probe 100 received from one or more flow sensors "$FS_1$", "$FS_2$" through "$FS_M$" may be used by the processor unit 82 to determine a desired fluid-flow rate. In such embodiments, flow data may be used by the processor unit 82 in conjunction with temperature data, or independently of temperature data, to determine a desired fluid-flow rate. The desired fluid-flow rate may be selected from a look-up table "$T_{X,Y}$" or determined by a computer algorithm stored within the memory device 8.

In some embodiments, an analog signal that is proportional to the temperature detected by a temperature sensor, e.g., a thermocouple, may be taken as a voltage input that can be compared to a look-up table "$T_{X,Y}$" for temperature and fluid-flow rate, and a computer program and/or logic circuitry associated with the processor unit 82 may be used to determine the needed duty cycle of the pulse width modulation (PWM) to control actuation of a valve (e.g., valve 52) to attain the desired fluid-flow rate. Processor unit 82 may be configured to execute a series of instructions such that the flow-control device 50 and the fluid-movement device 60 are cooperatively controlled by the processor unit 82, e.g., based on determination of a desired fluid-flow rate using temperature data and/or flow data, to selectively adjust the fluid-flow rate in a fluid-flow path (e.g., first coolant path 19) of the coolant supply system 11.

Feedback control system 14 may be adapted to control the flow-control device 50 to allow flow (e.g., valve 52 held open) for longer periods of time as the sensed temperature rises, and shorter periods of time as the sensed temperature falls. Electrosurgical system 10 may be adapted to override PWM control of the flow-control device 50 to hold the valve 52 open upon initial activation of the antenna assembly 112. For this purpose, a timer may be utilized to prevent the control device 50 from operating for a predetermined time interval (e.g., about one minute) after the antenna assembly 112 has been activated. In some embodiments, the predetermined time interval to override PWM control of the flow-control device 50 may be varied depending on setting, e.g., time and power settings, provided by the user. In some embodiments, the electrosurgical power generating source 28 may be adapted to perform a self-check routine that includes determination that the flow-control device 50 is open before enabling energy delivery between the electrosurgical power generating source 28 and the probe 100.

Figure 3:
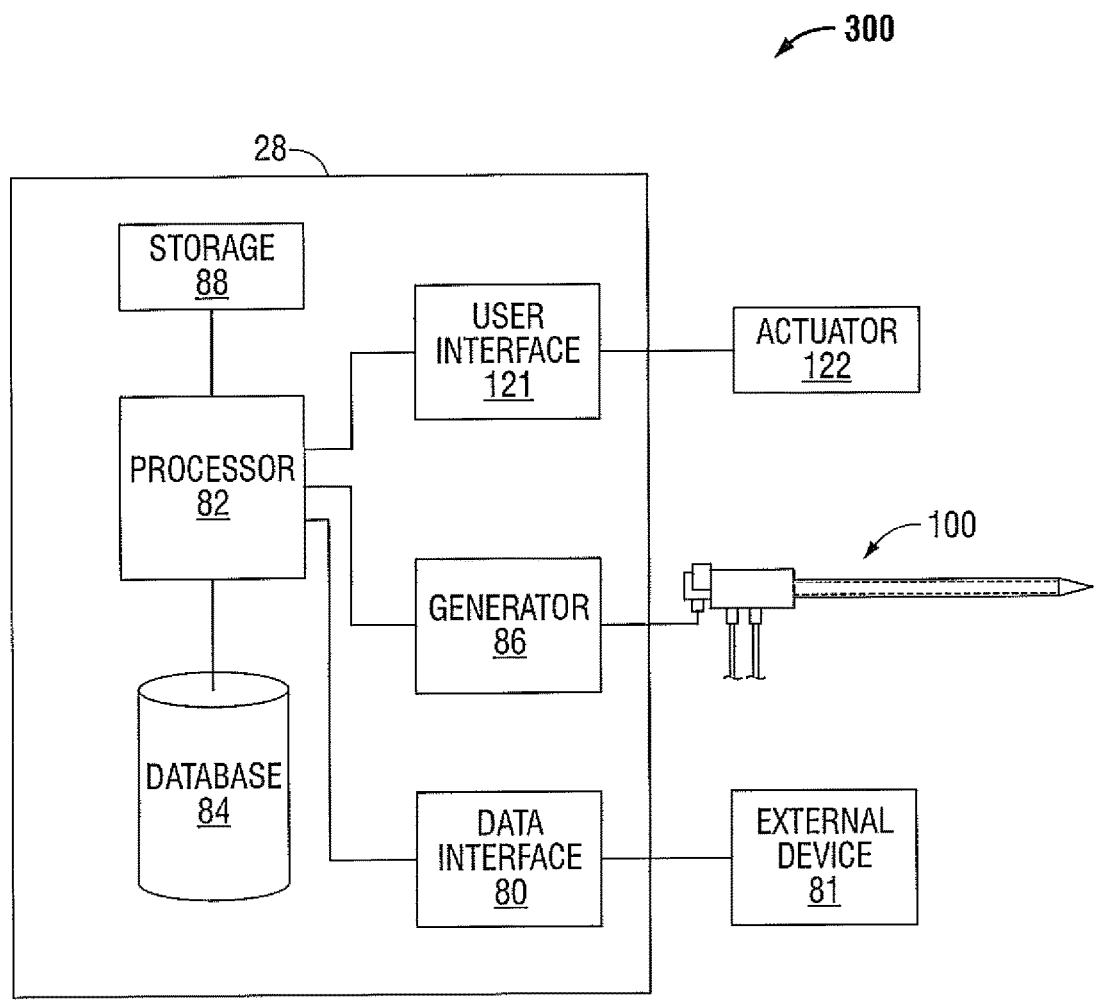
FIG. 3 is a block diagram of an electrosurgical system including an embodiment of the electrosurgical power generating source of FIG. 1 in accordance with the present disclosure.

FIG. 3 is a block diagram of an electrosurgical system 300 including an embodiment of the electrosurgical power generating source 28 of FIG. 1 that includes a generator module 86 in operable communication with a processor unit 82, a user interface 121 communicatively-coupled to the processor unit 82, and an actuator 122 communicatively-coupled to the user interface 121. Actuator 122 may be any suitable actuator, e.g., a footswitch, a handswitch, an orally-activated switch (e.g., a bite-activated switch and/or a breath-actuated switch), and the like. Probe 100 is operably-coupled, e.g., via transmission line 16 shown in FIG. 1, to an energy output of the generator module 86. User interface 121 may include an indicator unit 129 adapted to provide a perceptible sensory alert, which may be an audio, visual, such as an illuminated indicator (e.g., a single- or variably-colored LED indicator), or other sensory alarm.

In some embodiments, the generator module 86 is configured to provide energy of about 915 MHz. Generator module 86 may additionally, or alternatively, be configured to provide energy of about 2450 MHz (2.45 GHz) or about 5800 MHz (5.8 GHz). The present disclosure contemplates embodiments wherein the generator module 86 is configured to generate a frequency other than about 915 MHz or about 2450 MHz or about 5800 MHz, and embodiments wherein the generator module 86 is configured to generate variable frequency energy.

Processor unit 82 according to various embodiments is programmed to enable a user, via the user interface 121, to preview operational characteristics of an energy-delivery device, such as, for example, probe 100. Processor unit 82 may include any type of computing device, computational circuit, or any type of processor or processing circuit capable of executing a series of instructions that are stored in a memory, e.g., storage device 88 or external device 81.

In some embodiments, a storage device 88 is operably-coupled to the processor 82, and may include random-access memory (RAM), read-only memory (ROM), and/or non-volatile memory (e.g., NV-RAM, Flash, and disc-based storage). Storage device 88 may include a set of program instructions executable on the processor unit 82 for controlling the flow-control device 50 based on determination of a desired fluid-flow rate in accordance with the present disclosure. Electrosurgical power generating source 28 may include a data interface 80 that is configured to provide a communications link to an external device 81. In some embodiments, the data interface 80 may be any of a USB interface, a memory card slot (e.g., SD slot), and/or a network interface (e.g., 100BaseT Ethernet interface or an 802.11 "Wi-Fi" interface). External device 81 may be any of a USB device (e.g., a memory stick), a memory card (e.g., an SD card), and/or a network-connected device (e.g., computer or server).

Electrosurgical power generating source 28 may include a database 84 that is configured to store and retrieve energy applicator data, e.g., parameters associated with one or energy applicators, and/or other data (e.g., one or more lookup tables "$T_{X,Y}$"). Database 84 may also be maintained at least in part by data provided by an external device 81 via the data interface 80, e.g., energy applicator data may be uploaded from the external device 81 to the database 84 via the data interface 80.

Figure 4:
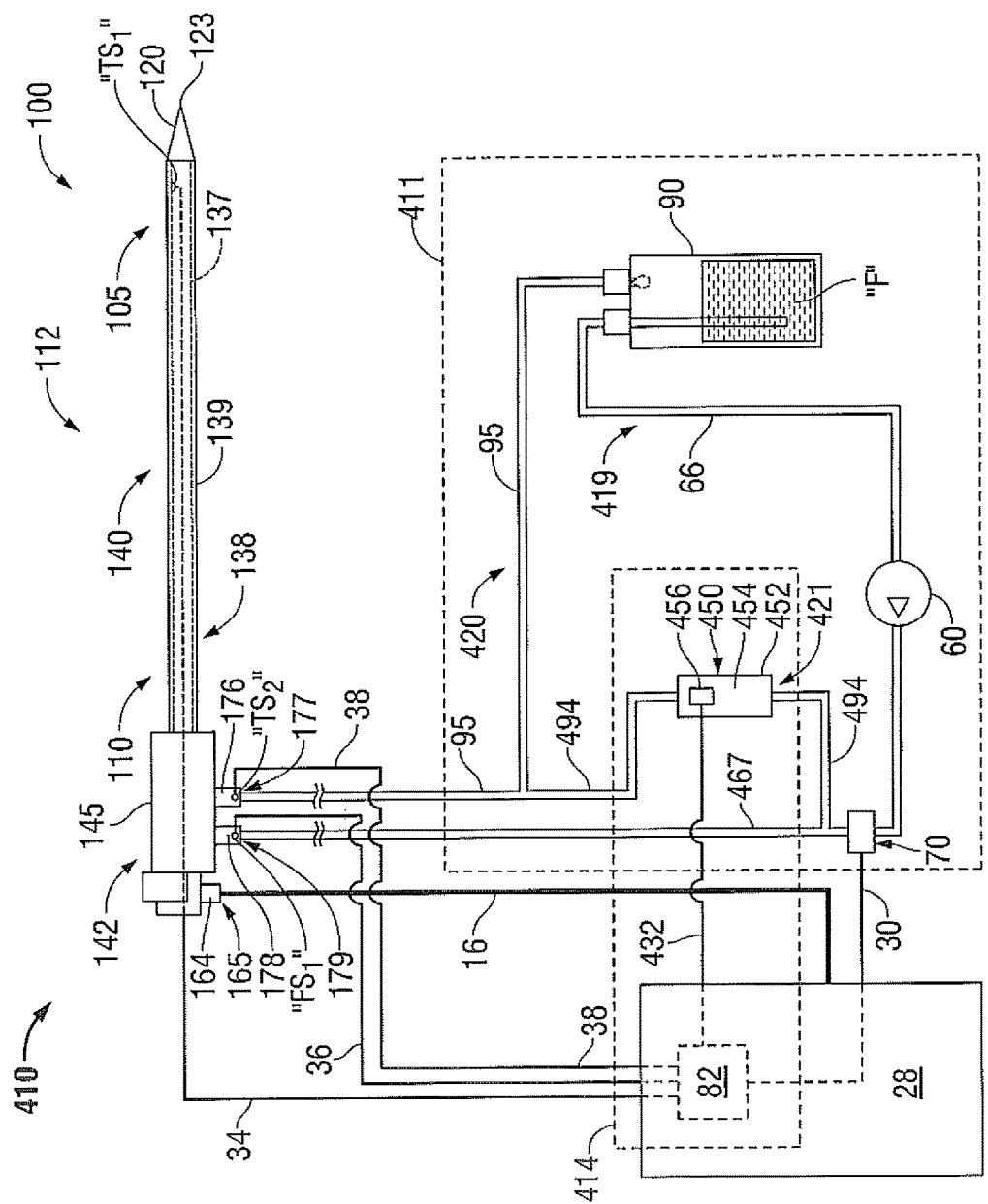
FIG. 4 is a schematic diagram of an electrosurgical system including the energy-delivery device of FIG. 1 shown with another embodiment of a feedback control system in operable connection with another embodiment of a fluid supply system in accordance with the present disclosure.

FIG. 4 shows an electrosurgical system 410 according to an embodiment of the present disclosure that includes the electrosurgical power generating source 28 and the probe 100 of FIG. 1 and a feedback control system 414 operably associated with a coolant supply system 411 adapted to provide coolant fluid "F" to the probe 100. In some embodiments, the feedback control system 414 is adapted to provide a thermal-feedback-controlled rate of fluid flow to the probe 100.

Coolant supply system 411 includes a substantially closed loop having a first coolant path 419 leading to the probe 100, a second coolant path 420 leading from the probe 100, and a diversion flow path 421 disposed in fluid communication with the first coolant path 419 and the second coolant path 420. Coolant supply system 411 generally includes the coolant source 90, fluid-movement device 60, first coolant supply line 66 leading from the coolant source 90 to the fluid-movement device 60, and the first coolant return line 95 leading to the coolant source 90 of the coolant supply system 11 of FIG. 1.

In contrast to the coolant supply system 11 of FIG. 1 that includes a flow-control device 50 disposed in fluid communication with the first coolant path 19 (fluidly-coupled to the inlet fluid port 179) and a pressure-relief device 40 disposed in fluid communication with the diversion flow path 21, the coolant supply system 411 shown in FIG. 4 includes a flow-control device 450 disposed in fluid communication with the diversion flow path 421 (fluidly-coupled to the coolant source 90). In the embodiment shown in FIG. 4, the coolant path 419 includes a second coolant supply line 467 leading from the fluid-movement device 60 to the inlet fluid port 179 defined in the connection hub 142, and the diversion flow path 421 includes a second coolant return line 494 fluidly-coupled to the second coolant supply line 467 and the first coolant return line 95, wherein the flow-control device 450 is disposed in fluid communication with the second coolant return line 494.

Feedback control system 414 includes a processor unit, e.g., processor unit 82 associated with the electrosurgical power generating source 28, or a standalone processor (not shown), operably associated with the flow-control device 450. Flow-control device 450 may include any suitable device capable of regulating or controlling the rate of fluid flow passing though the flow-control device 450. In the embodiment shown in FIG. 4, the flow-control device 450 includes a valve 452 including a valve body 454 and an electromechanical actuator 456 operatively coupled to the valve body 454. In some embodiments, the actuator 456 is operably associated with the processor unit 82, e.g., via a transmission line 432 or via wireless connection.

Processor unit 82 may be configured to control the flow-control device 450 by activating the actuator 456 to selectively adjust the fluid-flow rate in the diversion flow path 421 to effect a desired change in the fluid-flow rate in the first coolant path 419 leading to the probe 100. In some embodiments, the processor unit 82 may be configured to control the flow-control device 450 by activating the actuator 456 to selectively adjust the fluid-flow rate in the diversion flow path 421 based on determination of a desired fluid-flow rate using data received from one or more temperature sensors (e.g., two sensors "$TS_1$" and "$TS_2$") and/or data received from one or more flow sensors (e.g., one sensor "$FS_1$").

In some embodiments, the electrosurgical system 410 includes one or more pressure sensors (e.g., pressure transducer 70) disposed in fluid communication with one or more fluid-flow paths (e.g., first coolant path 419) of the coolant supply system 411. In the embodiment shown in FIG. 4, the pressure transducer 70 is disposed in fluid communication with the first coolant path 419 located between the fluid-movement device 60 and the flow-control device 450.

Figure 5:
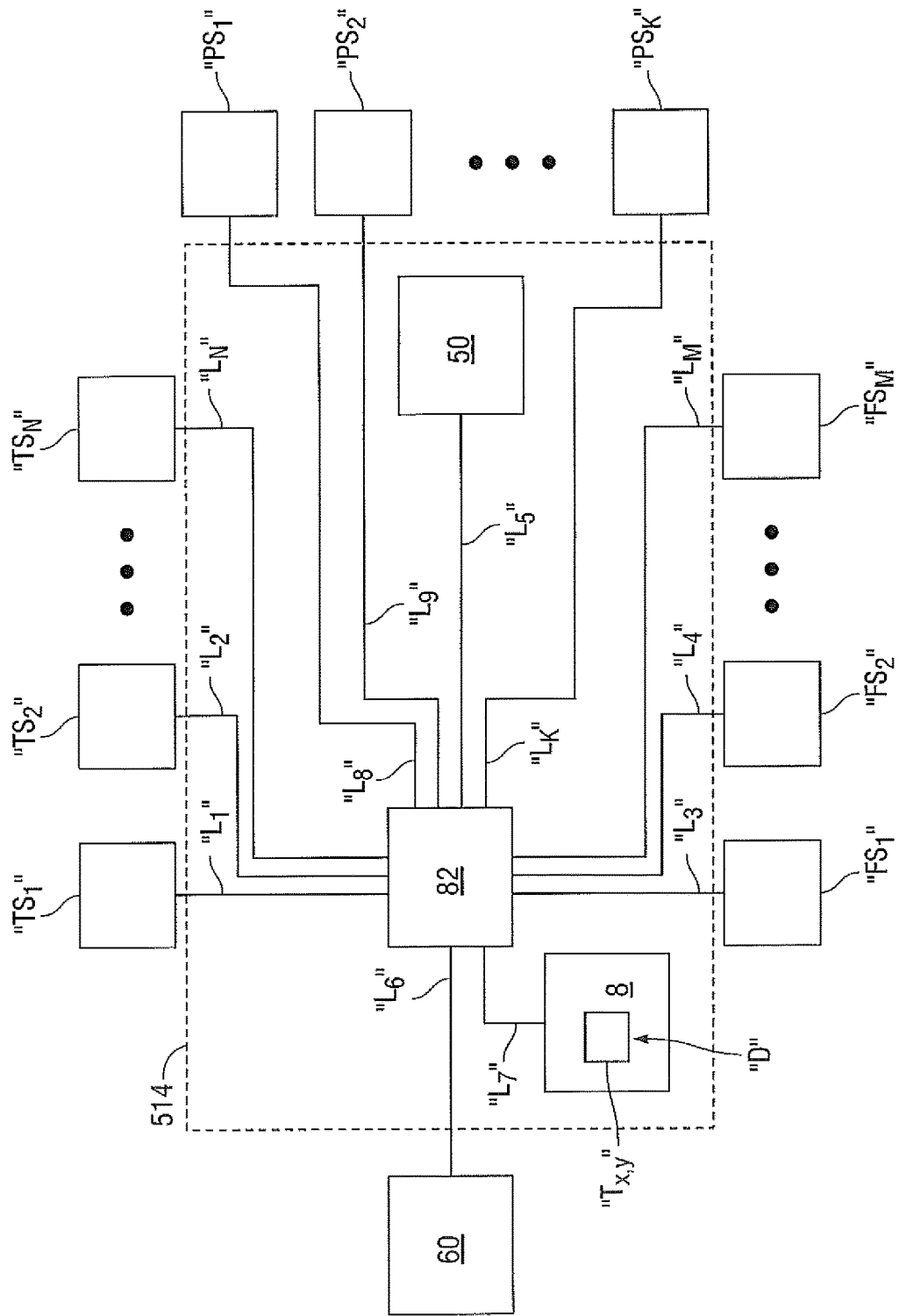
FIG. 5 is a schematic diagram of a feedback control system in accordance with another embodiment of the present disclosure.

FIG. 5 schematically illustrates a feedback control system 514 according to an embodiment of the present disclosure that includes the processor unit 82. Feedback control system 514 is similar to the feedback control system 14 of FIG. 2, except for the addition of pressure sensors "$PS_1$", "$PS_2$" through "$PS_K$", where K is an integer, and description of elements in common with the feedback control system 14 of FIG. 2 is omitted in the interests of brevity.

Processor unit 82 may be configured to enable the electrosurgical power generating source 28 for activating the probe 100 based on determination that the pressure level of fluid in one or more fluid-flow paths of the coolant supply system 11 is above a predetermined threshold using pressure data received from one or more pressure sensors "$PS_1$", "$PS_2$" through "$PS_K$". The pressure data may be transmitted via transmission lines "$L_8$", "$L_9$" through "$L_K$" or wirelessly transmitted. Processor unit 82 may additionally, or alternatively, be configured to stop energy delivery from the electrosurgical power generating source 28 to the probe 100 based on determination that the pressure level in one or more fluid-flow paths of the coolant supply system 11 is above a predetermined threshold using pressure data received from one or more pressure sensors "$PS_1$", "$PS_2$" through "$PS_K$". Processor unit 82 may additionally, or alternatively, be configured to execute a series of instructions to control one or more operational parameters of an electrosurgical power generating source 28 based on determination of whether the pressure level of fluid in the probe 100 and/or conduit fluidly-coupled to the probe 100 is above a predetermined threshold using pressure data received from one or more pressure sensors "$PS_1$", "$PS_2$" through "$PS_K$".

Hereinafter, methods of directing energy to tissue using a fluid-cooled antenna assembly in accordance with the present disclosure are described with reference to FIGS. 6 and 7. It is to be understood that the steps of the methods provided herein may be performed in combination and in a different order than presented herein without departing from the scope of the disclosure. Embodiments of the presently-disclosed methods of directing energy to tissue may be implemented as a computer process, a computing system or as an article of manufacture such as a pre-recorded disk or other similar computer program product or computer-readable media. The computer program product may be a non-transitory, computer-readable storage media, readable by a computer system and encoding a computer program of instructions for executing a computer process.

Figure 6:
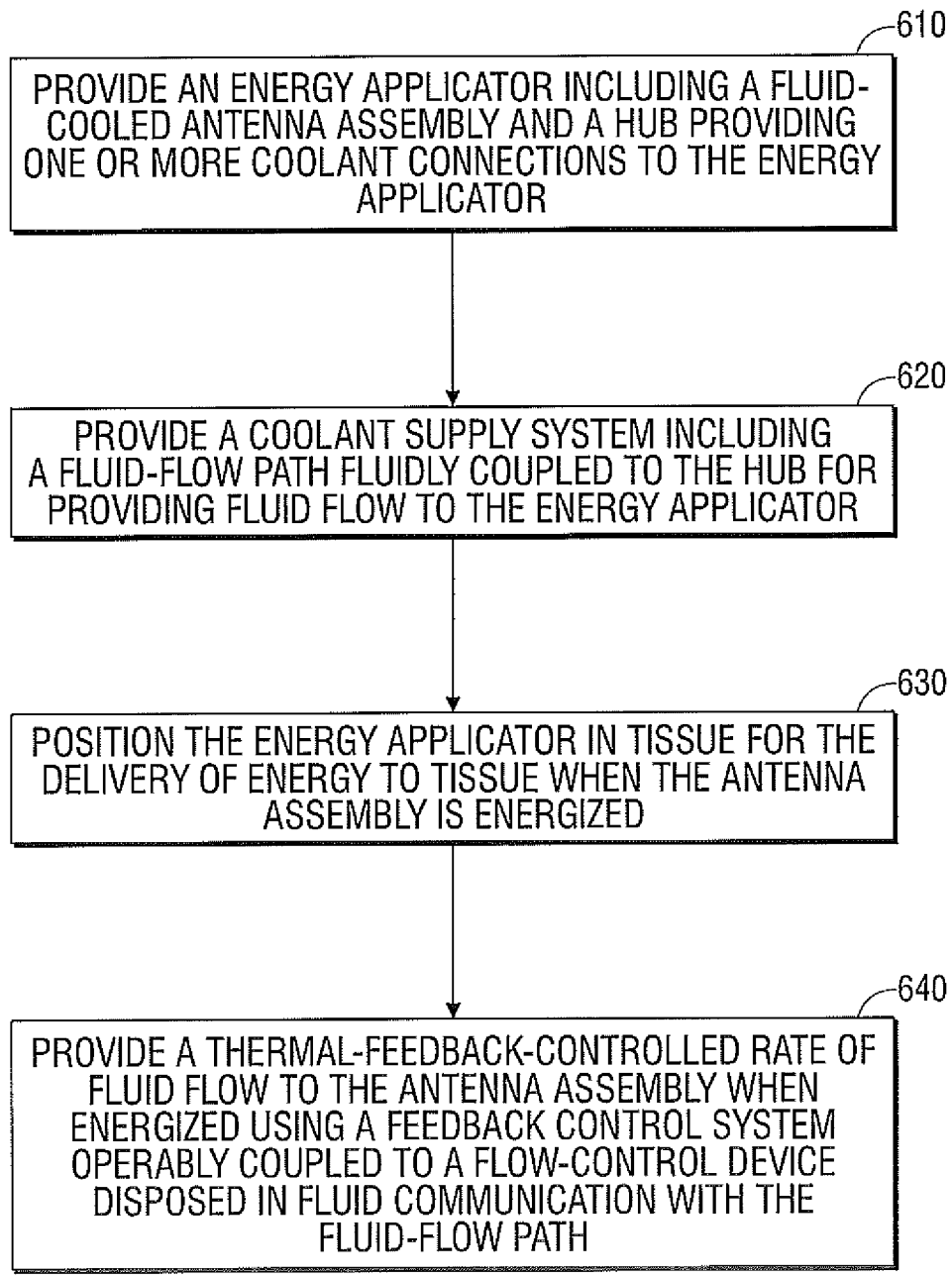
FIG. 6 is a flowchart illustrating a method of directing energy to tissue using a fluid-cooled antenna assembly in accordance with an embodiment of the present disclosure.

FIG. 6 is a flowchart illustrating a method of directing energy to tissue using a fluid-cooled antenna assembly according to an embodiment of the present disclosure. In step 610, an energy applicator 100 is provided. The energy applicator 100 includes an antenna assembly 112 and a hub 142 providing one or more coolant connections (e.g., inlet fluid port 179 shown in FIG. 1) to the energy applicator 100.

In step 620, a coolant supply system 11 (or coolant supply system 411 shown in FIG. 4) is provided. The coolant supply system 11 includes a fluid-flow path 19 fluidly-coupled to the hub 142 for providing fluid flow to the energy applicator 100. In some embodiments, the first coolant path 19 includes a first coolant supply line 66 leading from a coolant source 90 to a fluid-movement device 60, a second coolant supply line 67 leading from the fluid-movement device 60 to a flow-control device 50, and a third coolant supply line 68 leading from the flow-control device 50 to the inlet fluid port 179.

Coolant source 90 may be any suitable housing containing a reservoir of coolant fluid "F". Coolant fluid "F" may be any suitable fluid that can be used for cooling or buffering the energy applicator 100, e.g., deionized water, or other suitable cooling medium. Coolant fluid "F" may have dielectric properties and may provide dielectric impedance buffering for the antenna assembly 112.

In step 630, the energy applicator 100 is positioned in tissue for the delivery of energy to tissue when the antenna assembly 112 is energized. The energy applicator 100 may be inserted directly into tissue, inserted through a lumen, e.g., a vein, needle, endoscope or catheter, placed into the body during surgery by a clinician, or positioned in the body by other suitable methods. The energy applicator 100 may be configured to operate with a directional radiation pattern.

Electrosurgical energy may be transmitted from an energy source 28 through the antenna assembly 112 to tissue. The energy source 28 may be any suitable electrosurgical generator for generating an output signal. In some embodiments, the energy source 28 is a microwave energy source, and may be configured to provide microwave energy at an operational frequency from about 300 MHz to about 10 GHz. In some embodiments, the energy source 28 supplies power having a selected phase, amplitude and frequency.

In step 640, a thermal-feedback-controlled rate of fluid flow is provided to the antenna assembly 112 when energized, using a feedback control system 14 operably-coupled to a flow-control device 50 disposed in the fluid-flow path 19 leading to the energy applicator 100.

Figure 7:
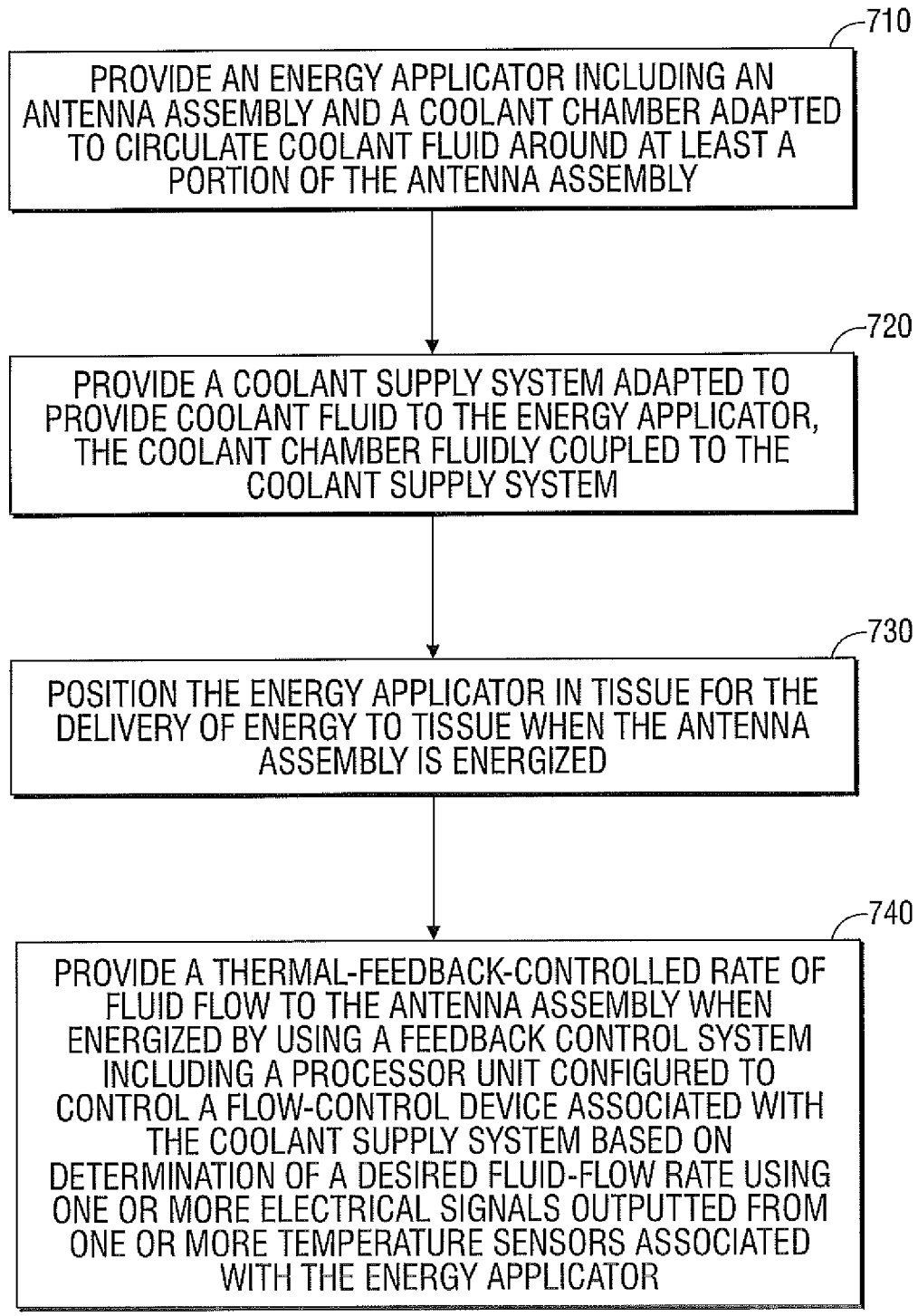
FIG. 7 is a flowchart illustrating a method of directing energy to tissue using a fluid-cooled antenna assembly in accordance with another embodiment of the present disclosure.

FIG. 7 is a flowchart illustrating a method of directing energy to tissue using a fluid-cooled antenna assembly according to an embodiment of the present disclosure. In step 710, an energy applicator 100 is provided. The energy applicator 100 includes an antenna assembly 112 and a coolant chamber 137 adapted to circulate coolant fluid "F" around at least a portion of the antenna assembly 112.

In step 720, a coolant supply system that is adapted to provide coolant fluid "F" to the energy applicator 100 is provided. The energy applicator 100 may be used in conjunction with coolant supply systems in various configurations. The coolant chamber 137 of the energy applicator 100 may be fluidly-coupled to a coolant supply system 11 according to an embodiment shown in FIG. 1 that includes a flow-control device 50 disposed in fluid communication with a first coolant path 19 (e.g., fluidly-coupled to the energy applicator 100 to provide fluid flow from a coolant source 90 to the energy applicator 100).

Alternatively, the coolant chamber 137 may be fluidly-coupled to a coolant supply system 411 according to an embodiment shown in FIG. 4 that includes a flow-control device 450 disposed in fluid communication with a third coolant path 421 disposed in fluid communication with a first coolant path 419 (e.g., fluidly-coupled to the energy applicator 100 to provide fluid flow from a coolant source 90 to the energy applicator 100) and a second coolant path 420 (e.g., fluidly-coupled to the energy applicator 100 to provide fluid flow from the energy applicator 100 to the coolant source 90).

In step 730, the energy applicator 100 is positioned in tissue for the delivery of energy to tissue when the antenna assembly 112 is energized. The energy applicator 100 may be inserted into or placed adjacent to tissue to be treated.

In step 740, a feedback control system 14 (or 414) including a processor unit 82 communicatively-coupled to one or more temperature sensors, e.g., one temperature sensor "$TS_1$", associated with the energy applicator 100 is used to provide a thermal-feedback-controlled rate of fluid flow to the antenna assembly 112 when energized. Processor unit 82 may be configured to control a flow-control device 50 (or 450) associated with the coolant supply system 11 (or 411) based on determination of a desired fluid-flow rate using one or more electrical signals outputted from the one or more temperature sensors "$TS_1$". Feedback control system 14 (or 414) may utilize data "D" (e.g., data representative of a mapping of temperature data to settings for properly adjusting one or more operational parameters of the flow-control device 50 (or 450) to achieve a desired temperature and/or desired ablation) stored in a look-up table "$T_{X,Y}$", or other data structure, to determine the desired fluid-flow rate.

In some embodiments, the processor unit 82 is communicatively-coupled to one or more pressure sensors 70 disposed in fluid communication with one or more fluid-flow paths (e.g., first coolant path 19) of the coolant supply system 11 (or 411). Processor unit 82 may be configured to enable an electrosurgical generator 28 for activating the energy applicator 100 based on determination that a sensed pressure level in the one or more fluid-flow paths is above a predetermined threshold using at least one electrical signal outputted from the one or more pressure sensors 70.

Processor unit 82 may additionally, or alternatively, be configured to control one or more operating parameters associated with the electrosurgical generator 28 based on determination that a sensed pressure level in the one or more fluid-flow paths (e.g., first coolant path 19) is below a predetermined threshold using at least one electrical signal outputted from the one or more pressure sensors 70. Examples of operating parameters associated with the electrosurgical power generating source 28 include without limitation temperature, impedance, power, current, voltage, mode of operation, and duration of application of electromagnetic energy.

In some embodiments, the coolant supply system 11 includes a fluid-movement device 60 disposed in fluid communication with the first coolant path 19, and may include a second coolant path 20 (e.g., fluidly-coupled to the energy applicator 100 to allow fluid flow to return to the coolant source 90) and a third coolant path 21 disposed in fluid communication with the first coolant path 19 and the second coolant path 20. A pressure-relief device 40 may be disposed in fluid communication with the third coolant path 21 and may allow the fluid-movement device 60 to run at a substantially constant speed and/or under a near-constant load (head pressure) regardless of the selective adjustment of the fluid-flow rate in the first coolant path 19.

The above-described systems for thermal-feedback-controlled rate of fluid flow to electrosurgical devices and methods of directing energy to tissue using a fluid-cooled antenna assembly may be used in conjunction with a variety of electrosurgical devices adapted for treating tissue. Embodiments may be used in conjunction with electrosurgical devices adapted to direct energy to tissue, such as ablation probes, e.g., placed percutaneously or surgically, and/or ablation devices suitable for use in surface ablation applications.

The above-described systems including a feedback control system adapted to provide a thermal-feedback-controlled rate of fluid flow to an energy applicator disposed in fluid communication with a coolant supply system may be suitable for a variety of uses and applications, including medical procedures, e.g., tissue ablation, resection, cautery, vascular thrombosis, treatment of cardiac arrhythmias and dysrhythmias, electrosurgery, etc.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of directing energy to tissue by using a fluid-cooled antenna assembly of an energy applicator, the method comprising:
    connecting the energy applicator to a hub, the hub coupled to a coolant supply system for providing fluid to the antenna assembly of the energy applicator, the coolant supply system having a coolant source, a first coolant supply line, a second coolant supply line, and a third coolant supply line in fluid communication with the coolant source, the first coolant supply line connected between the coolant source and a fluid-movement device, the second coolant supply line directly connected between a pressure transducer and the fluid-movement device, and the third coolant supply line directly connected between a flow-control device and the antenna assembly;
    positioning the energy applicator in tissue;
    activating the energy applicator via an electrosurgical generator;
    measuring a temperature of the fluid in the antenna assembly;
    controlling a thermal-feedback-controlled rate of fluid flow based on the measured temperature of the fluid in the antenna assembly;
    providing fluid to the antenna assembly at the thermal-feedback-controlled rate of fluid flow using a feedback control system including the flow-control device, the flow control device including a valve and an electromechanical actuator, and the feedback control system including a processor unit; and
    connecting the pressure transducer to the valve, the pressure transducer disposed within the coolant supply system;
    wherein the pressure transducer outputs a signal at a pressure below a burst pressure of a pressure relief valve to indicate to the electrosurgical generator that the fluid-cooled antenna assembly has coolant flowing therethrough and wherein the processor unit triggers a shut-off of the electrosurgical generator based on pressure levels of the coolant in the fluid-cooled antenna assembly; and wherein the processor unit outputs a signal indicative of an error code if a predetermined time elapses between energy delivery to the fluid-cooled antenna assembly and detection of the signal outputted by the pressure transducer.

2. The method of directing energy to tissue by using the fluid-cooled antenna assembly of claim 1, wherein the providing step further includes controlling the flow-control device by activating the electro-mechanical actuator to selectively adjust the rate of fluid-flow in response to at least one electrical signal received from at least one temperature sensor which performs the measuring of the temperature of the fluid in the antenna assembly.

3. The method of directing energy to tissue by using the fluid-cooled antenna assembly of claim 2, wherein the at least one temperature sensor is disposed within a distal radiating portion of the antenna assembly.

4. The method of directing energy to tissue by using the fluid-cooled antenna assembly of claim 2, wherein the at least one temperature sensor is disposed within a fluid return port defined in the hub.

5. The method of directing energy to tissue by using the fluid-cooled antenna assembly of claim 2, wherein the processor unit is incorporated within the electrosurgical generator and communicatively-coupled to the electro-mechanical actuator of the flow-control device.

6. The method of directing energy to tissue by using the fluid-cooled antenna assembly of claim 5, wherein the processor unit is further communicatively-coupled to at least one flow sensor.

7. The method of directing energy to tissue by using the fluid-cooled antenna assembly of claim 1, wherein the electro-mechanical actuator is controlled by pulse width modulation (PWM) techniques.

8. A method of directing energy to tissue by using a fluid-cooled antenna assembly of an energy applicator, the method comprising:

connecting the energy applicator to a coolant supply system adapted to circulate coolant fluid around at least a portion of the antenna assembly, the coolant supply system having a coolant source, a first coolant supply line, a second coolant supply line, and a third coolant supply line in fluid communication with the coolant source, the first coolant supply line connected between the coolant source and a fluid-movement device, the second coolant supply line directly connected between a pressure transducer and the fluid-movement device, and the third coolant supply line directly connected between a flow-control device and the antenna assembly;

positioning the energy applicator in tissue;

activating the energy applicator via an electrosurgical generator;

measuring a temperature of the coolant fluid in the antenna assembly;

controlling a thermal-feedback-controlled rate of fluid flow based on the measured temperature of the coolant fluid in the antenna assembly;

providing coolant fluid to the antenna assembly at the thermal-feedback-controlled rate of fluid flow using a feedback control system including a processor unit configured to control the flow-control device, the flow control device having a valve and an electro-mechanical actuator by activating the electro-mechanical actuator to selectively adjust the rate of fluid-flow in response to at least one electrical signal received from at least one temperature sensor associated with the energy applicator; and connecting a pressure transducer with to the valve, the pressure transducer disposed within the coolant supply system;

wherein the pressure transducer outputs a signal at a pressure below a burst pressure of a pressure relief valve to indicate to the electrosurgical generator that the fluid-cooled antenna assembly has coolant flowing therethrough and wherein the processor unit triggers a shut-off of the electrosurgical generator based on pressure levels of the coolant in the fluid-cooled antenna assembly; and wherein the processor unit outputs a signal indicative of an error code if a predetermined time elapses between energy delivery to the fluid-cooled antenna assembly and detection of the signal outputted by the pressure transducer.

9. The method of directing energy to tissue by using the fluid-cooled antenna assembly of claim 8, wherein the electro-mechanical actuator is controlled by pulse width modulation (PWM) techniques.

10. The method of directing energy to tissue by using the fluid-cooled antenna assembly of claim 8, wherein the pressure transducer allows the fluid-movement device to operate under a near-constant load.

11. The method of directing energy to tissue by using the fluid-cooled antenna assembly of claim 8, wherein the coolant supply system includes a closed loop configuration such that coolant fluid does not contact tissue, the closed loop configuration having a first coolant path leading to the antenna assembly from the coolant source and a second coolant path leading from the antenna assembly to the coolant source, the first coolant path formed by the first, second, and third coolant supply lines.

12. The method of directing energy to tissue by using the fluid-cooled antenna assembly of claim 8, wherein the processor unit is further configured to control at least one operating parameter associated with the electrosurgical generator.

13. The method of directing energy to tissue by using the fluid-cooled antenna assembly of claim 12, wherein the at least one operating parameter associated with the electrosurgical generator is selected from the group consisting of temperature, impedance, power, current, voltage, mode of operation, and duration of application of electromagnetic energy.

* * * * *